(12) United States Patent
Berman et al.

(10) Patent No.: US 7,062,013 B2
(45) Date of Patent: Jun. 13, 2006

(54) X-RAY REFLECTOMETRY OF THIN FILM LAYERS WITH ENHANCED ACCURACY

(75) Inventors: David Berman, Kiryat Tivon (IL); Alex Dikopoltsev, Haifa (IL); Dileep Agnihotri, Round Rock, TX (US)

(73) Assignee: Jordan Valley Applied Radiation Ltd., Migdal (IL)

( * ) Notice: Subject to any disclaimer, the term of this patent is extended or adjusted under 35 U.S.C. 154(b) by 209 days.

(21) Appl. No.: 10/689,314

(22) Filed: Oct. 20, 2003

(65) Prior Publication Data

US 2004/0131151 A1 Jul. 8, 2004

Related U.S. Application Data

(60) Continuation-in-part of application No. 10/364,883, filed on Feb. 12, 2003, now Pat. No. 6,895,075, and a continuation-in-part of application No. 10/313,280, filed on Dec. 6, 2002, now Pat. No. 6,947,520, and a continuation-in-part of application No. 10/300,504, filed on Nov. 20, 2002, now Pat. No. 6,639,968, and a division of application No. 09/833,902, filed on Apr. 12, 2001, now Pat. No. 6,512,814.

(51) Int. Cl.
*G01T 1/36* (2006.01)

(52) U.S. Cl. .............................. 378/82; 378/70; 378/89
(58) Field of Classification Search ................ 378/70, 378/82, 89; 356/445
See application file for complete search history.

(56) References Cited

U.S. PATENT DOCUMENTS

| | | | |
|---|---|---|---|
| 4,725,963 A | 2/1988 | Taylor et al. | |
| 5,151,588 A | 9/1992 | Kiri et al. | |
| 5,574,284 A | 11/1996 | Farr | |
| 5,619,548 A | 4/1997 | Koppel | |
| 5,740,226 A | 4/1998 | Komiya et al. | |
| 5,923,720 A | 7/1999 | Barton et al. | |
| 5,949,847 A | 9/1999 | Terada et al. | |
| 6,192,103 B1 | 2/2001 | Wormington et al. | |
| 6,381,303 B1 | 4/2002 | Vu et al. | |
| 6,389,102 B1 | 5/2002 | Mazor et al. | |
| 6,453,006 B1 | 9/2002 | Koppel et al. | |
| 6,507,634 B1 | 1/2003 | Koppel et al. | |
| 6,512,814 B1 | 1/2003 | Yokhin et al. | |

(Continued)

OTHER PUBLICATIONS

Chihab et al., "New Apparatus for Grazing X-Ray Reflectometry in the Angle-Resolved Dispersive Mode", Journal of Applied Crystallography 22 (1989), p. 460.

(Continued)

*Primary Examiner*—Edward J. Glick
*Assistant Examiner*—Chih-Cheng Glen Kao
(74) *Attorney, Agent, or Firm*—Amster, Rothstein & Ebenstein LLP

(57) ABSTRACT

A method for inspection of a sample that includes a first layer having a known reflectance property and a second layer formed over the first layer. The method includes directing radiation toward a surface of the sample and sensing the radiation reflected from the surface so as to generate a reflectance signal as a function of elevation angle relative to the surface. A feature due to reflection of the radiation from the first layer is identified in the reflectance signal. The reflectance signal is calibrated responsively to the identified feature and to the known reflectance property of the first layer. The calibrated reflectance signal is analyzed to determine a characteristic of the second layer. Other enhanced inspection methods are disclosed, as well.

14 Claims, 6 Drawing Sheets

U.S. PATENT DOCUMENTS

| | | | |
|---|---|---|---|
| 6,535,575 B1 * | 3/2003 | Yokhin | 378/82 |
| 6,639,968 B1 * | 10/2003 | Yokhin et al. | 378/70 |
| 6,643,354 B1 | 11/2003 | Koppel et al. | |
| 6,711,232 B1 | 3/2004 | Janik | |
| 6,744,950 B1 | 6/2004 | Aleksoff | |
| 6,771,735 B1 | 8/2004 | Janik et al. | |
| 6,813,338 B1 | 11/2004 | Takata et al. | |
| 6,895,071 B1 * | 5/2005 | Yokhin et al. | 378/45 |
| 6,895,075 B1 * | 5/2005 | Yokhin et al. | 378/70 |
| 2001/0028699 A1 | 10/2001 | Iwasaki | |
| 2001/0043668 A1 | 11/2001 | Hayashi et al. | |
| 2002/0097837 A1 | 7/2002 | Fanton et al. | |
| 2002/0110218 A1 | 8/2002 | Koppel et al. | |
| 2003/0157559 A1 | 8/2003 | Omote et al. | |
| 2004/0052330 A1 | 3/2004 | Koppel et al. | |
| 2004/0218717 A1 | 11/2004 | Koppel et al. | |

OTHER PUBLICATIONS

XTF5011 Tube, Produced by Oxford Instruments of Scotts Valley, California. Jun. 1999.

Doubly-Bent Focusing Crystal Optic, Produced by XOS Inc., of Albany, New York, Jul. 2000.

Wiener et al., "Characterization of Titanium Nitride Layers by Grazing-Emission X-Ray Fluorescence Spectrometry", in Applied Surface Science 125 (1998), pp. 129-136.

Model S7032-0908N array, Produced by Hamamatsu, of Hamamatsu City, Japan, May 2000.

J. Spear, "Metrology for low-k materials", Silknet Aliance, 2003.

J.R. Levine Parrill, et al, "GISAXS—Glancing Incidence Small Angle X-ray Scattering", Journal de Physique IV 3 (Dec. 1993), pp. 411-417.

Jaklevic, et al., "High Rate X-Ray Fluorescence Analysis by Pulsed Excitation", IEEE Transactions on Nuclear Science NS-19:3 (1972), pp. 392-395.

Jaklevic, et al., "Small X-Ray Tubes for Energy Dispersive Analysis Using Semiconductor Spectrometers", Advances in X-Ray Analysis 15 (1972), pp. 266-275.

Jaklevic, et al., "Energy Dispersive X-Ray Fluorescence Spectrometry Using Pulsed X-Ray Excitation", Advances in X-Ray Analysis 19 (1976), pp. 253-265.

Wormington, Characterization of Pore Size Distribution in Low k Dielectrics Using X-ray Reflectivity, presented at the Sematech Gate Stack Engineering Workshop (Austin, Texas, May 2, 2002).

Ito, "X-ray Scattering Method for Determining Pore-Size Distribution in Low-k Thin Films", Presented at the International Sematech Ultra-Low-k Workshop (San Francisco, CA, Jun. 6-7, 2002).

N. Wu, et al, "Substepping and its Application to HST Imaging", Jul. 28, 2003.

* cited by examiner

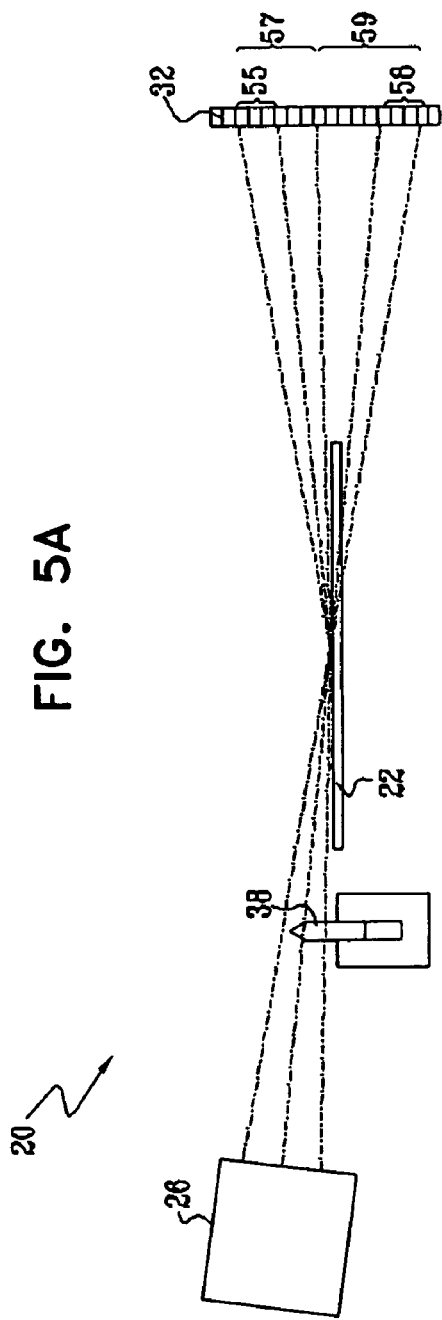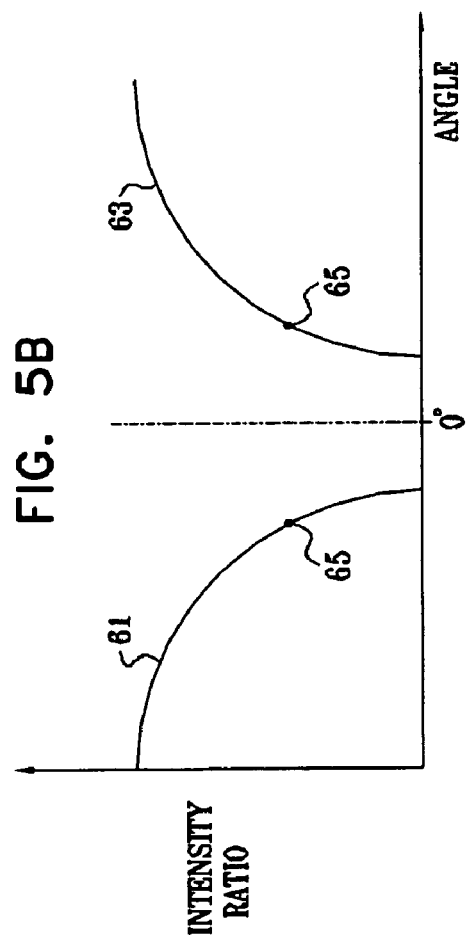

X-RAY REFLECTOMETRY OF THIN FILM LAYERS WITH ENHANCED ACCURACY

CROSS-REFERENCE TO RELATED APPLICATIONS

This application is a continuation-in-part of the following U.S. patent applications: U.S. patent application Ser. No. 10/300,504 filed Nov. 20, 2002, now U.S. Pat. No. 6,639,968, which is a division of U.S. patent application Ser. No. 09/833,902 filed Apr. 12, 2001, now U.S. Pat. No. 6,512,814; U.S. patent application Ser. No. 10/313,280 filed Dec. 6, 2002, now U.S. Pat. No. 6,947,520; and U.S. patent application Ser. No. 10/364,883 filed Feb. 12, 2003, now U.S. Pat. No. 6,895,075. These related applications are assigned to the assignee of the present patent application, and their disclosures are incorporated herein by reference.

FIELD OF THE INVENTION

The present invention relates generally to analytical instruments, and specifically to instruments and methods for thin film analysis using X-rays.

BACKGROUND OF THE INVENTION

X-ray reflectometry (XRR) is a well-known technique for measuring the thickness, density and surface quality of thin film layers deposited on a substrate. Conventional X-ray reflectometers are sold by a number of companies, among them Technos (Osaka, Japan), Siemens (Munich, Germany) and Bede Scientific Instrument (Durham, UK). Such reflectometers typically operate by irradiating a sample with a beam of X-rays at grazing incidence, i.e., at a small angle relative to the surface of the sample, near the total external reflection angle of the sample material. Measurement of X-ray intensity reflected from the sample as a function of angle gives a pattern of interference fringes, which is analyzed to determine the properties of the film layers responsible for creating the fringe pattern. The X-ray intensity measurements are commonly made using a position-sensitive detector, such as a proportional counter or an array detector, typically a photodiode array or charge-coupled device (CCD).

A method for analyzing the X-ray data to determine film thickness is described, for example, in U.S. Pat. No. 5,740,226, to Komiya et al., whose disclosure is incorporated herein by reference. After measuring X-ray reflectance as a function of angle, an average reflectance curve is fitted to the fringe spectrum. The average curve is based on a formula that expresses attenuation, background and surface roughness of the film. The fitted average reflectance curve is then used in extracting the oscillatory component of the fringe spectrum. This component is Fourier transformed to find the film thickness.

U.S. Pat. No. 5,619,548, to Koppel, whose disclosure is incorporated herein by reference, describes an X-ray thickness gauge based on reflectometric measurement. A curved, reflective X-ray monochromator is used to focus X-rays onto the surface of a sample. A position-sensitive detector, such as a photodiode detector array, senses the X-rays reflected from the surface and produces an intensity signal as a function of reflection angle. The angle-dependent signal is analyzed to determine properties of the structure of a thin film layer on the sample, including thickness, density and surface roughness.

U.S. Pat. No. 5,923,720, to Barton et al., whose disclosure is incorporated herein by reference, also describes an X-ray spectrometer based on a curved crystal monochromator. The monochromator has the shape of a tapered logarithmic spiral, which is described as achieving a finer focal spot on a sample surface than prior art monochromators. X-rays reflected or diffracted from the sample surface are received by a position-sensitive detector.

Another common method of X-ray reflectometric measurement is described, for example, in an article by Naudon et al., entitled "New Apparatus for Grazing X-ray Reflectometry in the Angle-Resolved Dispersive Mode," in *Journal of Applied Crystallography* 22 (1989), p. 460, which is incorporated herein by reference. A divergent beam of X-rays is directed toward the surface of a sample at grazing incidence, and a detector opposite the X-ray beam source collects reflected X-rays. A knife edge is placed close to the sample surface immediately above a measurement location in order to cut off the primary X-ray beam. A monochromator between the sample and the detector (rather than between the source and sample, as in U.S. Pat. No. 5,619,548) selects the wavelength of the reflected X-ray beam that is to reach the detector.

XRR may also be used in situ, within a deposition furnace, to inspect thin film layers in production on a semiconductor wafer, as described, for example, by Hayashi et al., in U.S. Patent Application Publication U.S. 2001/0043668 A1, whose disclosure is incorporated herein by reference. The furnace is provided with X-ray incidence and extraction windows in its side walls. The substrate upon which the thin film has been deposited is irradiated through the incidence window, and the X-rays reflected from the substrate are sensed through the X-ray extraction window.

SUMMARY OF THE INVENTION

Embodiments of the present invention provide methods and systems for performing XRR measurements with enhanced accuracy. These methods and systems are advantageous in analyzing thin film layers, and particularly in characterizing low-density materials, such as low-k porous dielectrics, that are deposited on a higher-density underlying layer, such as a silicon wafer.

In some embodiments of the present invention, the angular scale of an XRR fringe pattern generated by a thin film layer is calibrated based on the known reflectance properties of the underlying layer. The structure of the fringe pattern depends on the density, thickness and other properties of the thin film, but the pattern may also include a distinct shoulder at the critical angle for total external reflection from the underlying layer, particularly when the density of the thin film layer is lower than that of the underlying layer. This critical angle, in turn, is determined by the composition and density of the underlying layer. If the parameters of the underlying layer are known (as they are, for example, when the underlying layer is a silicon wafer substrate), the angular scale of the XRR fringe pattern can then be calibrated precisely based on the location of the shoulder.

In further embodiments of the present invention, an array of X-ray detector elements is used to measure XRR fringe patterns with sub-pixel resolution. For this purpose, the sample is irradiated by a converging X-ray beam. The array is positioned and oriented so that the elements of the array resolve the radiation reflected from the sample along an axis perpendicular to the plane of the sample. The array is then translated along the axis by an increment that is less than the pitch of the array, and the measurement is repeated. Preferably, the increment is equal an integer fraction of the pitch of the array (pitch/n, wherein n is an integer), and the measurement is repeated at n different positions of the array along the axis. The XRR measurements made at the different positions are combined, typically by interleaving the measurements taken at the different increments, in order to obtain a fringe spectrum with enhanced resolution.

Although the embodiments of the present invention described herein are directly mainly toward enhancing X-ray measurements on thin films, and particularly on films formed on semiconductor wafers, the principles of the present invention can similarly be used in other applications of X-ray reflectometry and scattering, as well as in other types of radiation-based analysis.

There is therefore provided, in accordance with an embodiment of the present invention, a method for inspection of a sample that includes a first layer having a known reflectance property and a second layer formed over the first layer, the method including:

directing radiation toward a surface of the sample;

sensing the radiation reflected from the surface so as to generate a reflectance signal as a function of elevation angle relative to the surface;

identifying a feature in the reflectance signal due to reflection of the radiation from the first layer;

calibrating the reflectance signal responsively to the identified feature and to the known reflectance property of the first layer; and analyzing the calibrated reflectance signal to determine a characteristic of the second layer.

Typically, the radiation includes X-rays, and sensing the radiation includes receiving the radiation at an array of detector elements having an array axis perpendicular to the surface.

In disclosed embodiments, identifying the feature includes finding a location of a shoulder in the reflectance signal corresponding to a critical angle for total external reflection from the first layer. Typically, calibrating the reflectance signal includes comparing the location of the shoulder to a known value of the critical angle, which is determined by a known density of the first layer. Calibrating the reflectance signal typically includes finding a zero angle in an angular scale of the reflectance signal based on the location of the shoulder and the known value of the critical angle.

In some embodiments, when the critical angle for total external reflection from the first layer is a first critical angle, analyzing the calibrated reflectance signal includes determining a calibrated value of a second critical angle for total external reflection from the second layer. Typically, the first and second layers have respective first and second densities, and analyzing the calibrated reflectance signal includes estimating the second density based on the calibrated value of the second critical angle, wherein the second density may be substantially less than the first density. In one embodiment, the first layer includes silicon, and the second layer includes a porous dielectric material.

There is also provided, in accordance with an embodiment of the present invention, apparatus for inspection of a sample that includes a first layer having a known reflectance property and a second layer formed over the first layer, the apparatus including:

a radiation source, which is adapted to direct X-rays toward a surface of the sample;

a detector assembly, which is arranged to sense the radiation reflected from the surface so as to generate a reflectance signal as a function of elevation angle relative to the surface; and a signal processor, which is coupled to receive and process the reflectance signal by identifying a feature in the reflectance signal due to reflection of the radiation from the first layer and calibrating the reflectance signal responsively to the identified feature and to the known reflectance property of the first layer, and to analyze the calibrated reflectance signal to determine a characteristic of the second layer.

There is additionally provided, in accordance with an embodiment of the present invention, apparatus for inspection of a sample, including:

a radiation source, which is adapted to direct X-rays toward a surface of the sample;

a detector assembly, which includes:

an array of detector elements, which are arranged along an array axis substantially perpendicular to the surface and are mutually separated by a predetermined pitch, and which are operative to receive the X-rays reflected from the surface and to generate signals responsively to the received radiation; and a motion element, which is coupled to shift the array of detector elements in a direction parallel to the array axis between at least first and second positions, which positions are separated one from another by an increment that is not an integer multiple of the pitch; and a signal processor, which is coupled to combine the signals generated by the detector assembly in at least the first and second positions so as to determine an X-ray reflectance of the surface as a function of elevation angle relative to the surface.

Typically, the signal processor is adapted to interleave the signals generated by the detector assembly in at least the first and second positions in order to determine the X-ray reflectance of the surface.

In disclosed embodiments, the increment is less than or equal to one half of the pitch.

Typically, the array includes a linear array, and the detector elements have a transverse dimension, perpendicular to the array axis, that is substantially greater than a pitch of the array. Alternatively, the array includes a two-dimensional matrix of the detector elements, and the detector assembly is adapted to bin the detector elements in respective rows of the array along a direction perpendicular to the array axis.

There is further provided, in accordance with an embodiment of the present invention, a method for inspection of a sample, including:

directing X-rays toward a surface of the sample;

configuring an array of detector elements, which are mutually separated by a predetermined pitch, to receive the X-rays reflected from the surface while resolving the received radiation along an array axis substantially perpendicular to the surface;

shifting the array of detector elements in a direction parallel to the array axis between at least first and second positions, which positions are separated one from another by an increment that is not an integer multiple of the pitch;

receiving at least first and second signals generated by the detector elements responsively to the X-rays received thereby in at least the first and second positions, respectively; and combining at least the first and second signals so as to determine an X-ray reflectance of the surface as a function of elevation angle relative to the surface.

There is moreover provided, in accordance with an embodiment of the present invention, a cluster tool for producing microelectronic devices, including:

a deposition station, which is adapted to deposit a thin-film layer over an underlying layer on a surface of a semiconductor wafer, the underlying layer having a known reflectance property; and an inspection station, including:
a radiation source, which is adapted to direct X-rays toward the surface of the wafer;
a detector assembly, which is arranged to sense the radiation reflected from the surface so as to generate a reflectance signal as a function of elevation angle relative to the surface; and
a signal processor, which is coupled to receive and process the reflectance signal by identifying a feature in the reflectance signal due to reflection of the radiation from the underlying layer and calibrating the reflectance signal responsively to the identified feature and to the known reflectance property of the underlying layer, and to analyze the calibrated reflectance signal to determine a characteristic of the thin-film layer deposited by the deposition station.

There is furthermore provided, in accordance with an embodiment of the present invention, apparatus for producing microelectronic devices, including:

a production chamber, which is adapted to receive a semiconductor wafer;

a deposition device, which is adapted to deposit a thin-film layer over an underlying layer on a surface of the semiconductor wafer within the chamber, the underlying layer having a known reflectance property;

a radiation source, which is adapted to direct X-rays toward the surface of the semiconductor wafer in the chamber;

a detector assembly, which is arranged to sense the radiation reflected from the surface so as to generate a reflectance signal as a function of elevation angle relative to the surface; and a signal processor, which is coupled to receive and process the reflectance signal by identifying a feature in the reflectance signal due to reflection of the radiation from the underlying layer and calibrating the reflectance signal responsively to the identified feature and to the known reflectance property of the underlying layer, and to analyze the calibrated reflectance signal to determine a characteristic of the thin-film layer deposited by the deposition device.

There is also provided, in accordance with an embodiment of the present invention, a cluster tool for producing microelectronic devices, including:

a deposition station, which is adapted to deposit a thin-film layer on a surface of a semiconductor wafer; and an inspection station, including:
a radiation source, which is adapted to direct X-rays toward the surface of the wafer;
a detector assembly, which includes:
an array of detector elements, which are arranged along an array axis substantially perpendicular to the surface and are mutually separated by a predetermined pitch, and which are operative to receive the X-rays reflected from the surface and to generate signals responsively to the received radiation; and
a motion element, which is coupled to shift the array of detector elements in a direction parallel to the array axis between at least first and second positions, which positions are separated one from another by an increment that is not an integer multiple of the pitch; and
a signal processor, which is coupled to combine the signals generated by the detector assembly in at least the first and second positions so as to determine an X-ray reflectance of the thin-film layer as a function of elevation angle relative to the surface.

There is additionally provided, in accordance with an embodiment of the present invention, apparatus for producing microelectronic devices, including:

a production chamber, which is adapted to receive a semiconductor wafer;

a deposition device, which is adapted to deposit a thin-film layer on a surface of the semiconductor wafer within the chamber;

a radiation source, which is adapted to direct X-rays toward the surface of the semiconductor wafer in the chamber;

a detector assembly, which includes:
an array of detector elements, which are arranged along an array axis substantially perpendicular to the surface and are mutually separated by a predetermined pitch, and which are operative to receive the X-rays reflected from the surface and to generate signals responsively to the received radiation; and
a motion element, which is coupled to shift the array of detector elements in a direction parallel to the array axis between at least first and second positions, which positions are separated one from another by an increment that is not an integer multiple of the pitch; and
a signal processor, which is coupled to combine the signals generated by the detector assembly in at least the first and second positions so as to determine an X-ray reflectance of thin-film layer as a function of elevation angle relative to the surface.

There is further provided, in accordance with an embodiment of the present invention, a method for inspection of a sample, including:

directing radiation from a radiation source in a first predetermined position toward a radiation sensor in the second predetermined position;

sensing the radiation that is directly incident on the radiation sensor from the radiation source so as to generate a first direct signal as a function of elevation angle, while a shutter is positioned so as to cut off the radiation at a predetermined cutoff angle;

sensing the radiation that is directly incident on the radiation sensor from the radiation source so as to generate a second direct signal as a function of the elevation angle, while the shutter is positioned so as not to cut off the radiation at the predetermined cutoff angle;

introducing a sample between the radiation source in the first predetermined position and the radiation sensor in the second predetermined position, so that the radiation is incident on a surface of the sample;

sensing the radiation reflected from the surface of the sample onto the radiation sensor so as to generate a first reflectance signal as a function of the elevation angle, while the shutter is positioned so as to cut off the radiation at the predetermined cutoff angle;

sensing the radiation reflected from the surface of the sample onto the radiation sensor so as to generate a second reflectance signal as a function of the elevation angle, while the shutter is positioned so as not to cut off the radiation at the predetermined cutoff angle; and comparing a first ratio between the first direct signal and the second direct signal with a second ratio between the first reflectance signal and the second reflectance signal in order to find the elevation angle of a tangent to the surface.

Typically, the method includes analyzing the first and second reflectance signals so as to determine a property of a thin film layer at the surface of the sample.

In a disclosed embodiment, comparing the first ratio with the second ratio includes finding a first elevation angle at which the first ratio has a given value and a second elevation angle at which the second ratio has the given value, and determining the elevation angle of the tangent to the surface to be an average of the first and second elevation angles. Additionally or alternatively, the method includes taking a difference between the first and second elevation angles so as to determine a minimum elevation angle below which the shutter cuts off the radiation.

There is moreover provided, in accordance with an embodiment of the present invention, apparatus for inspection of a sample, including:

a radiation source in a first predetermined position, which is adapted to generate radiation;

a shutter, which is positionable so as to cut off the radiation at a predetermined cutoff angle;

a motion stage, which is configured to position a sample so that the radiation generated by the radiation source is incident on a surface of the sample;

a radiation sensor in a second predetermined position, which is adapted to sense the radiation so as to generate signals responsive to the radiation incident on the radiation sensor as a function of elevation angle, the signals including:

a first direct signal responsive to the radiation that is directly incident on the radiation sensor from the radiation source while the shutter is positioned so as to cut off the radiation at the predetermined cutoff angle;

a second direct signal responsive to the radiation that is directly incident on the radiation sensor from the radiation source while the shutter is positioned so as not to cut off the radiation at the predetermined cutoff angle;

a first reflectance signal responsive to the radiation reflected from the surface of the sample onto the radiation sensor while the shutter is positioned so as to cut off the radiation at the predetermined cutoff angle; and a second reflectance signal responsive to the radiation reflected from the surface of the sample onto the radiation sensor while the shutter is positioned so as not to cut off the radiation at the predetermined cutoff angle; and a signal processor, which is coupled to compare a first ratio between the first direct signal and the second direct signal with a second ratio between the first reflectance signal and the second reflectance signal in order to find the elevation angle of a tangent to the surface.

It should be understood that the terms "first" and "second" are used above and in the claims arbitrarily. Thus, for example, these terms do not necessarily reflect the actual order in which the signals described above are received.

The present invention will be more fully understood from the following detailed description of the embodiments thereof, taken together with the drawings in which:

BRIEF DESCRIPTION OF THE DRAWINGS

FIG. 5A is a schematic side view of the system of FIG. 1, showing the angles subtended by an X-ray beam in different configurations of a shutter and sample in the system, in accordance with an embodiment of the present invention;

FIG. 5B is a schematic plot of X-ray measurement results used in determining a zero angle for incidence of X-rays on the sample in the system shown in FIG. 5A, in accordance with an embodiment of the present invention;

DETAILED DESCRIPTION OF EMBODIMENTS

Figure 1:
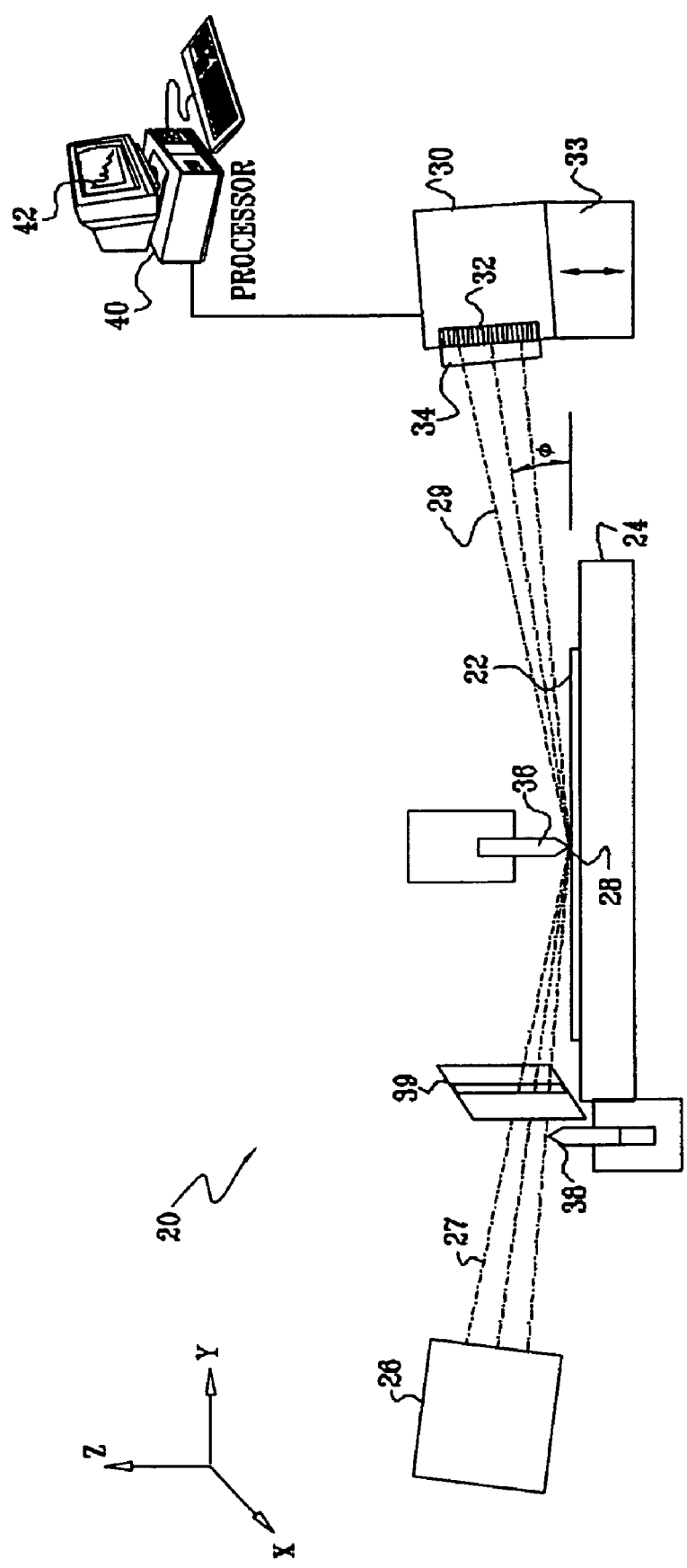
FIG. 1 is a schematic side view of a system for X-ray reflectometry (XRR) measurements, in accordance with an embodiment of the present invention.

Reference is now made to FIG. 1, which is a schematic side view of a system 20 for X-ray reflectometry (XRR), in accordance with an embodiment of the present invention. System 20 is similar to the XRR system described in the above-mentioned U.S. Pat. No. 6,512,814, with the addition of features and capabilities described herein.

A sample 22, such as a semiconductor wafer, to be evaluated by system 20 is mounted on a motion stage 24, allowing accurate adjustment of its position and orientation. An X-ray source 26, typically an X-ray tube with suitable monochromatizing optics (not shown), irradiates a small area 28 on sample 22. For example, the XTF5011 X-ray tube, produced by Oxford Instruments (Scotts Valley, Calif.), may be used for this purpose. The optics focus the radiation from the X-ray tube onto area 28 in a converging beam 27. A number of different optical configurations that may be used in source 26 are described in U.S. Pat. No. 6,381,303, whose disclosure is incorporated herein by reference. For example, the optics may comprise a curved crystal monochromator, such as the Doubly-Bent Focusing Crystal Optic, produced by XOS Inc., of Albany, N.Y. Other suitable optics are described in the above-mentioned U.S. Pat. Nos. 5,619,548 and 5,923,720. Further possible optical configurations will be apparent to those skilled in the art. A typical X-ray energy for reflectometric and scattering measurements in system 20 is about 8.05 keV (CuKa1). Alternatively, other energies may be used, such as 5.4 keV (CrKa1).

A dynamic knife edge 36 and shutter 38 are used to limit the angular extent of incident beam 27 of the X-rays in the vertical direction (i.e., perpendicular to the plane of sample 22), while a slit 39 may be used to limit the beam horizontally. The knife edge, shutter and slit together serve as a shutter assembly, for adjusting the transverse dimensions of beam 27. The configuration of the shutter assembly in FIG. 1 is shown by way of example, and alternative arrangements of X-ray optics for controlling the transverse dimensions of beam 27 in the manner described hereinbelow will be apparent to those skilled in the art and are considered to be within the scope of the present invention.

The use of knife edge 36 and shutter 38 in XRR measurements is described in detail in the above-mentioned U.S. Pat. No. 6,512,814. Briefly, for optimal detection of low-angle reflections, near 0°, shutter 38 is withdrawn outside the extent of incident beam 27, while knife edge 36 is positioned over area 28 and is lowered to reduce the effective vertical cross-section of the beam. As a result, the lateral dimension of the X-ray spot incident on area 28 is reduced. On the other hand, for effective detection of weaker, high-angle reflection, knife edge 36 is withdrawn from beam 27, while shutter 38 is positioned to cut off the low-angle portion of the beam. (Alternatively, the shutter may be positioned to cut off the low-angle portion of reflected beam 29.) In this manner, only the high-angle reflections from sample 22 reach the detector array, and not the strong low-angle reflections, thus enhancing the signal/background ratio of the high-angle measurement. During XRR measurements, slit 39 is typically wide open, in order to admit the full cone of converging rays and thus increase the signal/noise ratio of the reflectivity measurement.

A reflected beam 29 of X-rays from sample 22 is collected by a detector assembly 30. Typically, for XRR, assembly 30 collects reflected X-rays over a range of reflection angles in the vertical (elevation—ϕ) direction between about 0° and 3°, both below and above the critical angle of the sample for total external reflection. (For clarity of illustration, the angles shown in the figures are exaggerated, as is the elevation of source 26 and detector assembly 30 above the plane of sample 22 in FIG. 1.)

Assembly 30 comprises a detector array 32, such as a CCD array, as described hereinbelow. Although for simplicity of illustration, only a single row of detectors elements is shown in the figures, with a relatively small number of detector elements, array 32 generally includes a greater number of elements, arranged as either a linear array or a matrix (two-dimensional) array. Assembly 30 may comprise a translation element 33, of any suitable type known in the art, for shifting and aligning array 32 relative to sample 22. Assembly 30 further comprises a window 34 made of a suitable X-ray transparent material, such as beryllium, spaced in front of the detector array, between the array and the sample. Further details of the operation of array 32 are described below with reference to FIG. 2.

A signal processor 40 analyzes the output of assembly 30, so as to determine a distribution 42 of the flux of X-ray photons reflected from sample 22 as a function of angle at a given energy or over a range of energies. Typically, sample 22 has one or more thin surface layers, such as thin films, at area 28, so that distribution 42 as a function of elevation angle exhibits an oscillatory structure due to interference effects among reflected X-ray waves from the interfaces between the layers. Processor 40 analyzes characteristics of the angular distribution in order to determine characteristics of one or more of the surface layers of the sample, such as the thickness, density and surface quality of the layer, using methods of analysis described hereinbelow.

Figure 2:
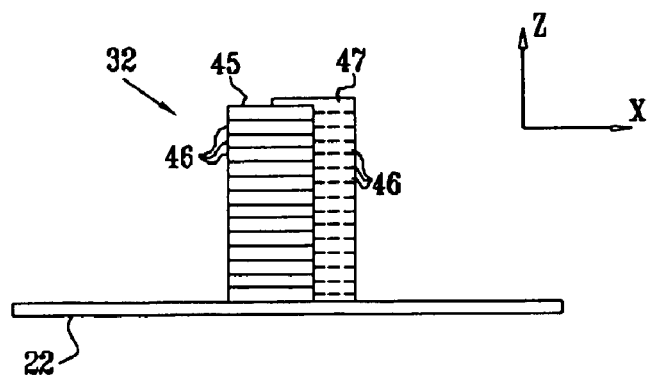
FIG. 2 is a schematic, frontal view of a detector array, configured for XRR, in accordance with an embodiment of the present invention.

FIG. 2 is a schematic frontal view of array 32, in accordance with an embodiment of the present invention. Array 32 is shown in this figure as comprising a single row of detector elements 46, with an array axis that is aligned along an axis perpendicular to the plane of sample 22. Elements 46 have a high aspect ratio, i.e., their width, in the direction transverse to the array axis, is substantially greater than their pitch along the axes. The high aspect ratio is useful in enhancing the signal/noise ratio of system 20, since array 32 is thus able to collect X-ray photons over a relatively wide area for each angular increment along the array axis. The dimensions of elements 46 are shown in the figures solely by way of example, however, and the principles of the present invention may be applied using elements of smaller or larger aspect ratio, depending on application needs and availability of suitable detector devices.

As noted above, array 32 may comprise either a linear CCD array or a matrix array, such as the model S7032-1008 array produced by Hamamatsu, of Hamamatsu City, Japan. This latter array comprises 1044×256 pixels, with an overall size of 25.4×6 mm. It is capable of being operated in a line-binning mode, using special hardware supplied for this purpose by Hamamatsu, so that multiple detector elements in each row of the array function effectively as a single element with high aspect ratio. In this case, although array 32 physically comprises a two-dimensional matrix of detector elements, functionally the array takes the form of a single line of detector elements, as shown in FIG. 2.

Alternatively, array 32 may comprise an array of PIN diodes with suitable readout circuits, possibly including integrated processing electronics, as described in U.S. Pat. No. 6,389,102, whose disclosure is incorporated herein by reference. This patent also describes alternative features of the array, including various geometrical configurations of the array (both one- and two-dimensional) and masking that may be applied to enhance the array's detection properties. These features are applicable to assembly 30 of the present patent application, as well. In any event, it will be understood that these detector types are described here by way of example, and detectors of any suitable type, dimension and number can be used.

In one aspect of the present invention, illustrated in FIG. 2, array 32 is shifted by small increments in the Z-direction, using translation element 33 (FIG. 1), for example. Two vertical positions 45 and 47 of array 32 are shown, separated by an increment in the Z-direction of one-half the pitch of the array, i.e., one-half the center-to-center separation of detector elements 46. (Although positions 45 and 47 are shown in FIG. 2 as being horizontally offset, as well, the horizontal offset is used solely for the purpose of clarity of illustration in this figure and is not necessary or desirable in XRR measurements.) In each position 45 and 47, source 26 is actuated, and assembly 30 captures the X-rays reflected from sample 22 as a function of the elevation angle. Assembly 30 may be operated in this manner to capture X-rays at more than two different vertical positions, typically with a smaller Z-direction increment between the positions. For example, three different positions separated by ⅓ the array pitch may be used.

The signals generated by assembly 30 in each different vertical position are input to processor 40, which combines the readings made at the different positions into a single spectrum. Essentially, the processor creates a "virtual array," with finer resolution than the actual, physical array 32. The signals in the virtual array can be derived, for example, simply by interleaving the readings made in the different array positions. Thus, for each "virtual pixel" in the virtual array, processor 40 selects the measurement value of a real pixel at the corresponding position in one of the actual measurements, alternating from one virtual pixel to the next among the readings made in the different measurement positions. In other words, assume the following read pixel readings were made in three successive positions of the array:

Position 1: R11, R21, R31, R41, . . .
Position 2: R12, R22, R32, R42, . . .
Position 3: R13, R23, R33, R43, . . .

The resultant virtual array will then contain the following values, at virtual pixels separated by ⅓ the actual array pitch:

R11, R12, R13, R21, R22, R23, R31, R32, R33, R41, . . .

Alternatively, other methods, such as signal differentiation or summing of the readings in the different array positions, may be used to extract XRR information from the individual, actual measurements before combining them, or to select the actual measurement result to be used in each pixel of the virtual array.

The resolution-enhancement techniques described hereinabove are useful particularly when the XRR spectrum has a fine structure with high spatial frequency, so that the fringe separation is comparable to or smaller than the array pitch. Alternatively, when the XRR spectrum is sufficiently strong and the fringes are well separated, it may be sufficient to measure the XRR signal at a single vertical position, such as position 45, in order to extract an acceptable spectrum.

Figure 3:
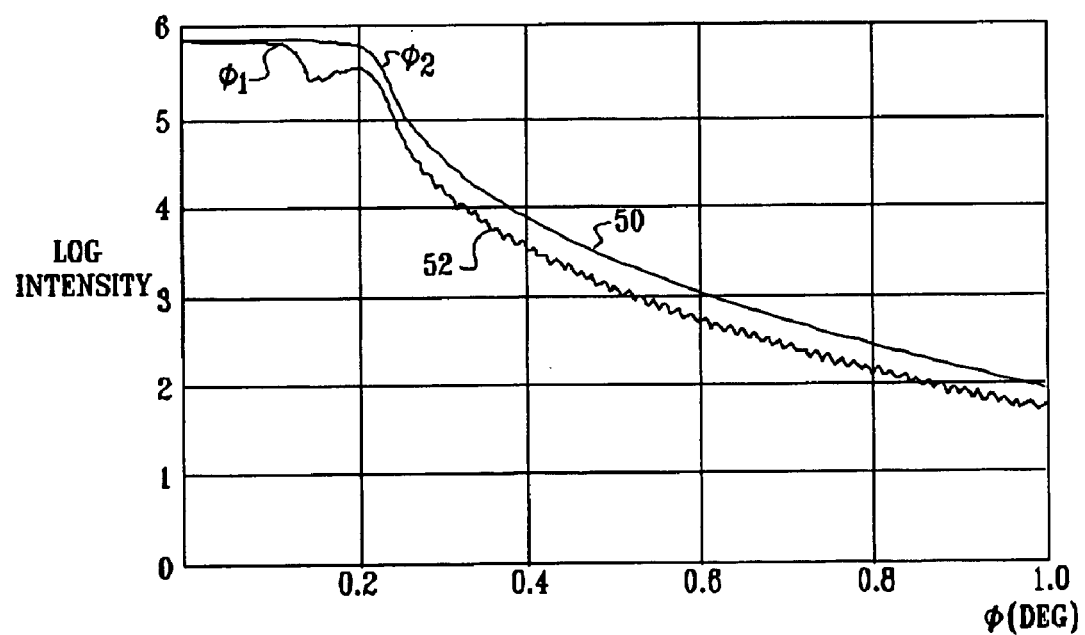
FIG. 3 is a schematic plot of XRR measurements, in accordance with an embodiment of the present invention.
Figure 4:
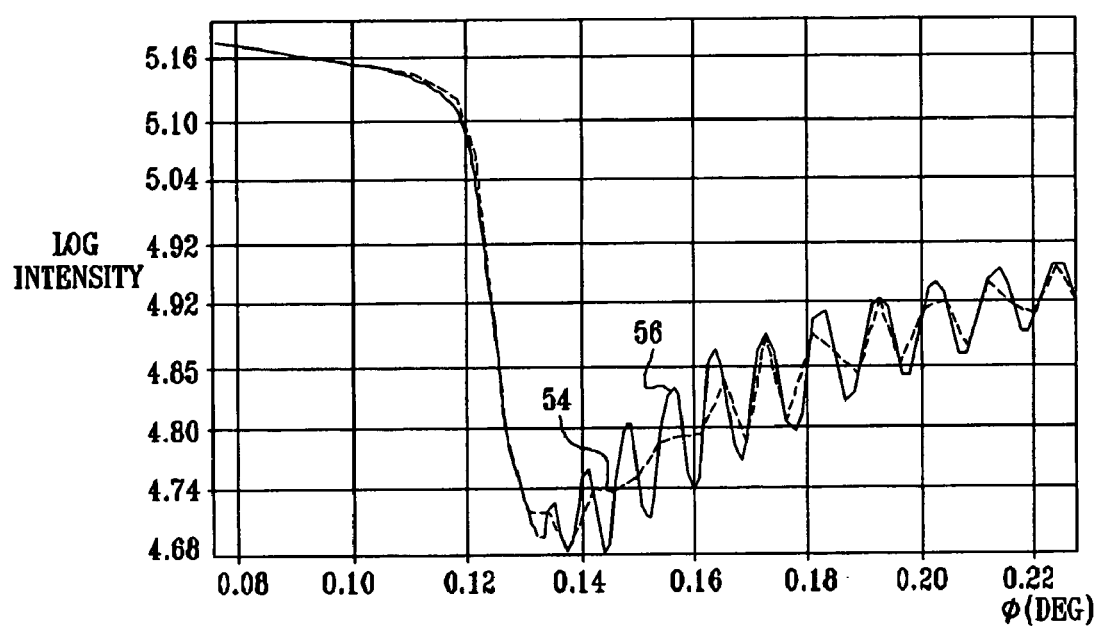
FIG. 4 is a schematic plot of XRR measurements, illustrating a method for acquiring XRR spectra with sub-pixel resolution, in accordance with an embodiment of the present invention.

FIGS. 3 and 4 are schematic plots of XRR measurements made using system 20, in accordance with an embodiment of the present invention. Plots of this sort may be generated using signals received at a single vertical position of array 32 or by combining signals from two or more different vertical positions, as described above. The plot in FIG. 3 shows the intensity of reflected X-rays received by array 32 in a single vertical position, as a function of the elevation angle φ, using Cu Kα (8.05 keV) radiation from source 26. FIG. 4, described below, shows the result of combining signals captured at multiple different vertical positions of array 32.

An upper curve 50 shows the reflection measured from a bare silicon wafer, while a lower curve 52 shows the reflection from a wafer on which a low-k porous dielectric film has been formed. Both curves have a shoulder at an angle marked in the figure as $\phi_2$, slightly greater than 0.2°. This angle corresponds to the critical angle for total external reflection from silicon. More precisely, for a standard silicon wafer with density 2.33 g/cm³, the critical angle at 8.05 keV is 0.227°. Therefore, once the location of the shoulder at $\phi_2$ is found, the zero point in the angular (horizontal) scale in the spectrum of FIG. 3 can be determined precisely, simply by going back 0.227° to the left of $\phi_2$. The scaling factor of the angular scale, in degrees per detector element 46, is given by $$\frac{180°}{\pi} \arctan\left(\frac{\text{array pitch}}{\text{focal dist}}\right) \cong \frac{180°}{\pi}\left(\frac{\text{array pitch}}{\text{focal dist}}\right),$$

wherein the focal distance is the distance from focal area 28 to array 32. Alternatively or additionally, the angular scale can be calibrated absolutely, based on the shoulder at $\phi_2$ but without reference to the array pitch and focal distance, using the method described in the above-mentioned U.S. patent application Ser. No. 10/313,280.

Above the critical angle, curve 52 shows an oscillatory structure, due mainly to reflections from the upper and lower surfaces of the low-k film. The period and amplitude of this oscillation may be analyzed to determine the thickness and surface quality of the low-k film and possibly other thin film layers below it on the wafer. A Fast Fourier Transform (FFT), for example, may be used to extract the relevant characteristics of the oscillation. Alternatively, a parametric curve fitting method may be used to give a more accurate determination of the film parameters. Methods for analyzing XRR signals such as curve 52 are described in greater detail in the above-mentioned U.S. Pat. No. 6,512,814.

The critical angle, and hence the location of the shoulder in the reflectance curve, is determined mainly by the density of the material from which the X-rays reflect. Since the porous, low-k dielectric layer that is deposited on the wafer has a substantially lower density than the silicon substrate, the critical angle of the porous layer is substantially smaller than that of the underlying silicon. Therefore, another shoulder is seen in curve 52, at a smaller angle marked in the figure as $\phi_1$, corresponding to the critical angle of the porous layer. The exact value of $\phi_1$ can be determined from the calibration of the angular scale described above, using the known value of $\phi_2$. Processor 40 is then able to determine the overall density of the porous material with high precision, based on the calibrated value of $\phi_1$. Since the intrinsic density of the dielectric material (in the absence of pores) is typically known, the total volume of pores, per unit volume of the porous layer, may be deduced as the difference between the known, intrinsic density of the dielectric material and the estimated overall density of the porous layer, based on the measured value of $\phi_1$.

FIG. 4 shows the intensity of reflected X-rays received by array 32 as a function of the elevation angle φ, showing the result of combining multiple measurements made at different vertical positions of the array. The angular scale in this figure is expanded relative to that of FIG. 3. A raw curve 54 shows a typical measurement made at a single vertical position of array 32. A combined curve 56 shows the result obtained by combining five measurements taken at different vertical positions of the array, which are offset one from the other in Z-direction increments of ⅕ of the array pitch. The pitch of the array is such that the angular separation between successive detector elements 46 is about 0.004°.

The period of the oscillatory pattern of the reflected radiation, as seen in curve 56, varies between about 0.007° and about 0.010°, which is near the Nyquist limit of array 32. Therefore, curve 54 fails to capture a portion of the true oscillatory structure, which appears in curve 56, and reproduces other portions of the structure with poor fidelity. On the other hand, when multiple measurements are combined, the portions of the oscillatory structure that are lost in curve 54 are captured successfully in other measurements. As a result, the effective resolution of array 32 is enhanced, as illustrated by curve 56. The enhancement gained in this manner may provide resolution that is effectively finer than the resolution of the X-ray optics that are used to cast the oscillatory pattern on array 32. As noted above, a theoretical model is fitted to curve 56 in order to determine parameters such as the thickness and surface quality of the surface layer on sample 22. Since the XRR signal is by nature complex and exhibits non-linear frequency variation as a function of angle, the added data points that are gained by shifting the array in the manner described above are useful in improving the fit and hence extracting more accurate values of the surface layer parameters.

Reference is now made to FIGS. 5A and 5B, which schematically illustrate a method for determining the zero angle of sample 22, in accordance with an embodiment of the present invention. FIG. 5A is a schematic side view of system 20, showing the angular spread of the X-ray beam generated by source 26 and incident on array 32 under different system conditions. The angular characteristics of the beam detected by array 32 under these different conditions are used in determining the zero angle of sample 22. The term "zero angle" in this context is used to refer to the elevation angle of a tangent to the surface of sample 22 at the point of incidence of the X-ray beam on the sample. This zero angle is equivalent to the zero point noted above in the spectra shown in FIG. 3. Unlike the method described above for finding the zero point in these spectra, however, the method illustrated by FIGS. 5A and 5B does not rely on any particular sort of layer structure on sample 22. The zero angle is found in the present context by identifying the detector element of array 32 that is aligned with the tangent to sample 22 (or in a virtual array created by the resolution enhancement technique described above, by finding the virtual pixel that is aligned with this tangent).

FIG. 5A shows four different beam configurations:

A narrow reflected beam 55, which is incident on array 32 when sample 22 is in place and shutter 38 is positioned to cut off the low-angle portion of the beam, as shown in the figure.

A broad reflected beam 57, extending roughly down to the zero angle of sample 22, when shutter 38 is withdrawn from the beam.

A narrow direct beam 58, which is incident on array 32 when sample 22 is removed from the X-ray beam path (so that there is no reflected beam), while shutter 38 is once again positioned to cut off the low-angle portion of the beam.

A broad direct beam 59, extending up to the zero angle of beam 57, and typically even beyond this zero angle, when both the shutter and the sample are removed from the X-ray beam.

Note that near the zero angle, the signal captured by array 32 due to beam 57 does not have a sharp cutoff, but rather increases gradually and not entirely smoothly. (For simplicity, this gradual increase is not shown in FIG. 3.) Therefore, it is difficult to determine the zero angle based on this signal alone.

FIG. 5B is a schematic plot of the results of measurements made by array 32 under irradiation by beams 55, 57, 58 and 59. The results are computed for each pixel on the horizontal (angular) axis as the ratio of the intensity value of the pixel due to one of the narrow beams to the value due to the corresponding one of the broad beams, i.e., RATIO=$I_{NARROW}/I_{BROAD}$. A left branch 61 of the plot, for elevation angles below the zero angle, is generated by computing the ratio of each pixel value measured when beam 58 is incident on array 32 to the value measured when beam 59 is incident. A right branch 63, for elevation angles above the zero angle, is given by the ratio of each pixel value measured when beam 55 is incident on the array to the value measured when beam 57 is incident.

As shown in FIG. 5B, the ratios for both positive and negative angles are typically zero in the vicinity of the zero angle, since shutter 38 cuts off beams 55 and 58 in this angular range. The ratios increase above zero at a cut-on angle, corresponding roughly to the angle at which shutter 38 intercepts the X-ray beam, growing gradually to a value of about one an angles away from the shutter edge. Branches 61 and 63 tend to be smooth curves, since local variations in the intensity values due to the narrow beam are typically canceled out by corresponding variations in the intensity values due to the broad beam. Therefore, the zero angle can be found accurately by taking the average angle between fifty-percent points 65 (at which the intensity ratio is 0.5). Alternatively, a curve fitting procedure may be applied to branches 61 and 63, and the fit parameters may be used to find the zero angle. The angular position of shutter 38 is given by half the angular distance between points 65. As a further alternative, curve 63 may be mirrored about a point on the horizontal axis so that it overlaps with curve 61. The mirroring point that gives the best overlap between the two curves is identified as the zero angle.

The method exemplified by FIGS. 5A and 5B can be used to find the zero angle at substantially any point on the surface of sample 22, independently of the nature of the sample and of the presence or absence of certain types of surface layers on the sample. This method for finding the zero angle is particularly useful, for example, in X-ray reflectometry of semiconductor wafers, which tend to warp, so that the zero angle varies over the surface of the wafer. The method remains valid even if the incident X-ray beam is not uniform, and regardless of any angular variation in the reflected beam (as long as the reflectivity varies continuously as a function of angle). This method may be combined with the resolution enhancement method described above with reference to FIGS. 2–4 (in which signals are acquired at different positions of array 32) in order to determine the zero angle with even greater accuracy.

Another advantage of the present method is that it can be carried out in concert with the actual XRR measurements, substantially without interrupting the measurement procedure. The measurements of direct beams 58 and 59 can be made whenever sample 22 is absent from system 20, typically in between measurements of different samples. The measurements of reflected beams 55 and 57 can be made in parallel to the XRR measurements. For example, when the surface layer density of the sample is greater than about 1.5 g/cm$^3$, the angular range between about 0.15° and 4° is used for XRR analysis, while the range between 0° and 0.15° can be used for zero angle calibration.

To acquire the data used to create branch 63, for example, shutter 38 is advanced to cut off the low-angle portion of the X-ray beam, below about 0.1°, and a reflection signal is acquired from array 32 over an exposure time of about 1–2 sec. The shutter is then retracted, and a further reflection signal is acquired from the array. The signals may be normalized in proportion to the ratio of exposure duration in the two shutter positions. The ratio of the normalized curves is calculated to find branch 63. A similar procedure is used to create branch 61.

Figure 6:
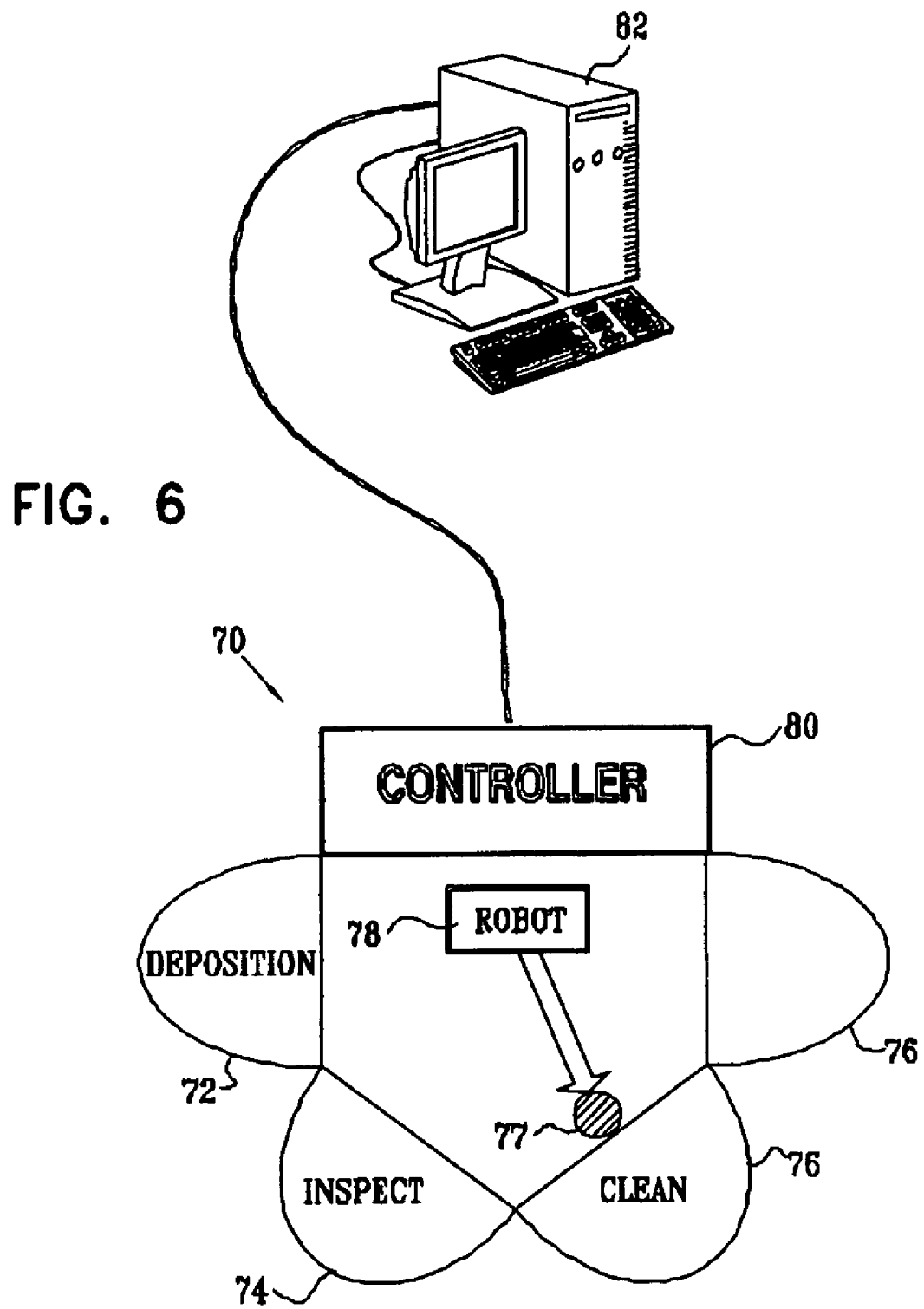
FIG. 6 is a schematic top view of a cluster tool for semiconductor device fabrication, including an inspection station in accordance with an embodiment of the present invention.

FIG. 6 is a schematic top view of a cluster tool 70 for use in semiconductor device fabrication, in accordance with an embodiment of the present invention. The cluster tool comprises multiple stations, including a deposition station 72, for depositing thin films on a semiconductor wafer 77, an inspection station 74, and other stations 76, as are known in the art, such as a cleaning station. Inspection station 74 is constructed and operates in a manner similar to system 20, as described hereinabove. A robot 78 transfers wafer 77 among stations 72, 74, 76, . . . , under the control of a system controller 80. Operation of tool 70 may be controlled and monitored by an operator using a workstation 82, coupled to controller 80.

Inspection station 74 is used to perform X-ray inspection of wafers by XRR before and after selected steps in production processes carried out by deposition station 72 and other stations in tool 70. In an exemplary embodiment, deposition station 72 is used to create porous thin films, such as porous low-k dielectric layers, on wafer 77, and inspection station 74 performs XRR evaluation, as described above. This arrangement allows early detection of process deviations and convenient adjustment and evaluation of process parameters on production wafers, using controller 80 and possibly workstation 82. The techniques described above for finding zero angles and enhancing detection resolution may also be used in station 74.

Figure 7:
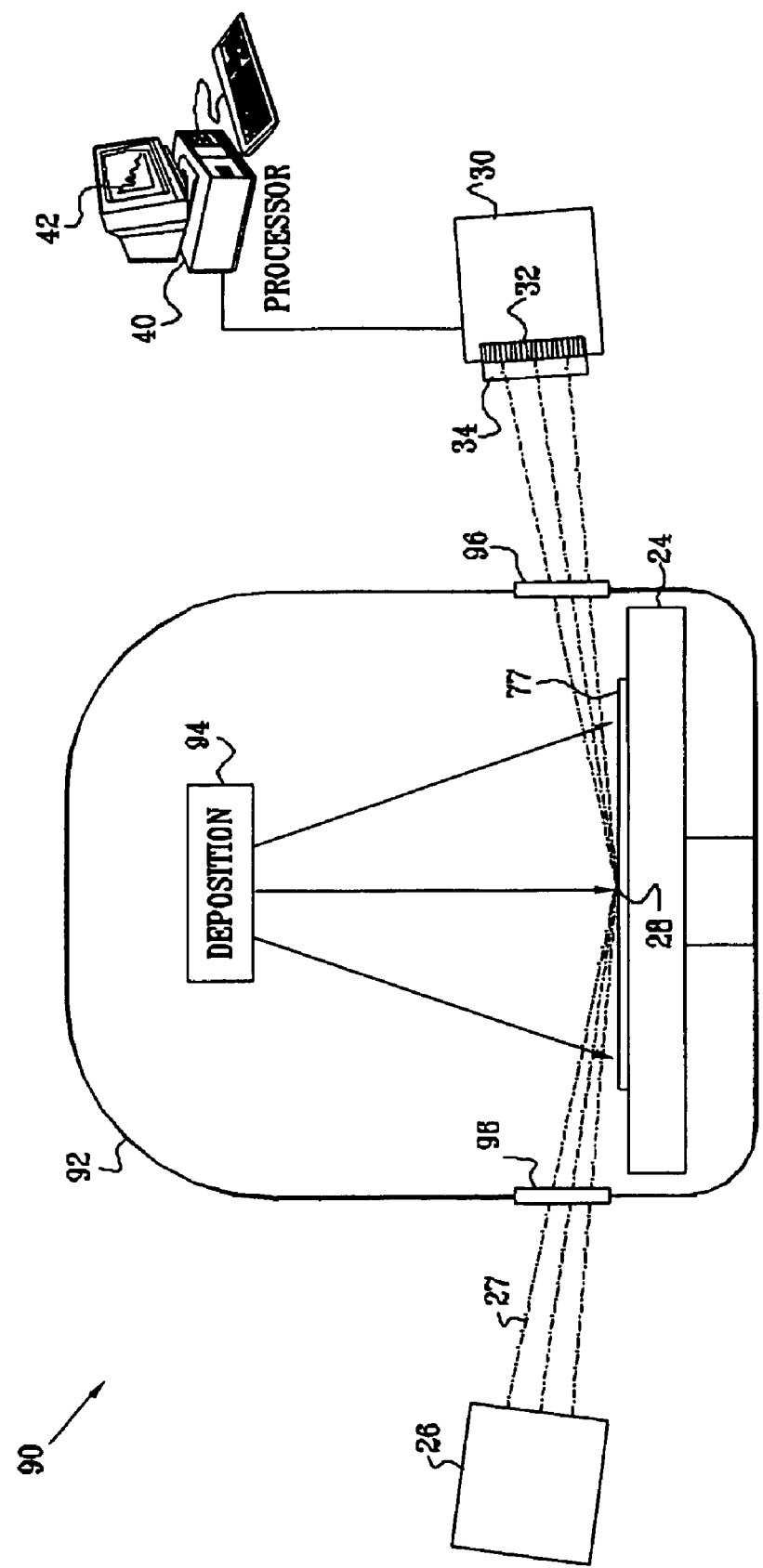
FIG. 7 is a schematic side view of a semiconductor processing chamber with X-ray inspection capability, in accordance with an embodiment of the present invention.

FIG. 7 is a schematic side view of a system 90 for semiconductor wafer fabrication and in situ inspection, in accordance with another embodiment of the present invention. System 90 comprises a vacuum chamber 92, containing deposition apparatus 94, for creating thin films on wafer 77, as is known in the art. The wafer is mounted on motion stage 24 within chamber 92. The chamber typically comprises X-ray windows 96, which may be of the type described in the above-mentioned Patent Application Publication US 2001/0043668 A1. X-ray source 26 irradiates area 28 on wafer 77 via one of windows 96, in the manner described above. The shutter, knife edge and slit shown in FIG. 1 are omitted from FIG. 7 for the sake of simplicity, but typically, elements of this sort are integrated into source 26 or within chamber 92.

X-rays reflected from area 28 are received by array 32 in detector assembly 30 via another one of windows 96. Processor 40 receives signals from detector assembly 30, and processes the signals in order to assess characteristics of thin-film layers in production within chamber 92. The results of this assessment may be used in controlling deposition apparatus 94 so that the films produced by system 90 have desired characteristics, such as thickness, density and porosity. The techniques described above for finding zero angles and enhancing detection resolution may also be used in chamber 92.

Although the embodiments described above deal mainly with determining porosity characteristics of low-k dielectric layers on semiconductor wafers, the principles of the present invention can similarly be used in other X-ray reflectometry applications, as well as in other types of radiation-based analysis, using not only X-rays, but also other ionizing radiation bands. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for inspection of a sample, comprising:
   directing radiation from a radiation source in a first predetermined position toward a radiation sensor in a second predetermined position;
   sensing the radiation that is directly incident on the radiation sensor from the radiation source so as to generate a first direct signal as a function of elevation angle, while a shutter is positioned so as to cut off the radiation at a predetermined cutoff angle;
   sensing the radiation that is directly incident on the radiation sensor from the radiation source so as to generate a second direct signal as a function of the elevation angle, while the shutter is positioned so as not to cut off the radiation at the predetermined cutoff angle;
   introducing a sample between the radiation source in the first predetermined position and the radiation sensor in the second predetermined position, so that the radiation is incident on a surface of the sample;
   sensing the radiation reflected from the surface of the sample onto the radiation sensor so as to generate a first reflectance signal as a function of the elevation angle, while the shutter is positioned so as to cut off the radiation at the predetermined cutoff angle;
   sensing the radiation reflected from the surface of the sample onto the radiation sensor so as to generate a second reflectance signal as a function of the elevation angle, while the shutter is positioned so as not to cut off the radiation at the predetermined cutoff angle; and
   comparing a first ratio between the first direct signal and the second direct signal with a second ratio between the first reflectance signal and the second reflectance signal in order to find the elevation angle of a tangent to the surface.

2. The method according to claim 1, wherein the radiation comprises X-rays.

3. The method according to claim 1, wherein the radiation sensor comprises an array of detector elements having an array axis perpendicular to the surface of the sample.

4. The method according to claim 3, wherein sensing the radiation to determine the direct and reflectance signals comprises:
   translating the array between at least first and second positions along a direction parallel to the array axis;
   generating first and second signals due to the radiation received by the detector elements in at least the first and second positions; and
   combining at least the first and second signals so as to generate an enhanced signal.

5. The method according to claim 1, and comprising analyzing the first and second reflectance signals so as to determine a property of a thin film layer at the surface of the sample.

6. The method according to claim 1, wherein comparing the first ratio with the second ratio comprises finding a first elevation angle at which the first ratio has a given value and a second elevation angle at which the second ratio has the given value, and determining the elevation angle of the tangent to the surface to be an average of the first and second elevation angles.

7. The method according to claim 6, and comprising taking a difference between the first and second elevation angles so as to determine a minimum elevation angle below which the shutter cuts off the radiation.

8. Apparatus for inspection of a sample, comprising:
   a radiation source in a first predetermined position, which is adapted to generate radiation;
   a shutter, which is positionable so as to cut off the radiation at a predetermined cutoff angle;
   a motion stage, which is configured to position a sample so that the radiation generated by the radiation source is incident on a surface of the sample;
   a radiation sensor in a second predetermined position, which is adapted to sense the radiation so as to generate signals responsive to the radiation incident on the radiation sensor as a function of elevation angle, the signals comprising:
      a first direct signal responsive to the radiation that is directly incident on the radiation sensor from the radiation source while the shutter is positioned so as to cut off the radiation at the predetermined cutoff angle;
      a second direct signal responsive to the radiation that is directly incident on the radiation sensor from the radiation source while the shutter is positioned so as not to cut off the radiation at the predetermined cutoff angle;
      a first reflectance signal responsive to the radiation reflected from the surface of the sample onto the radiation sensor while the shutter is positioned so as to cut off the radiation at the predetermined cutoff angle; and a second reflectance signal responsive to the radiation reflected from the surface of the sample onto the radiation sensor while the shutter is positioned so as not to cut off the radiation at the predetermined cutoff angle; and a signal processor, which is coupled to compare a first ratio between the first direct signal and the second direct signal with a second ratio between the first reflectance signal and the second reflectance signal in order to find the elevation angle of a tangent to the surface.

9. The apparatus according to claim 8, wherein the radiation comprises X-rays.

10. The apparatus according to claim 8, wherein the radiation sensor comprises an array of detector elements having an array axis perpendicular to the surface of the sample.

11. The apparatus according to claim 10, wherein the radiation sensor comprises a motion element, which is adapted to translate the array between at least first and second positions along a direction parallel to the array axis, so that the array generates at least first and second signals due to the radiation received by the detector elements in the first and second positions, and wherein the signal processor is adapted to combine at least the first and second signals in order to generate an enhanced signal.

12. The apparatus according to claim 8, wherein the signal processor is adapted to analyze the first and second reflectance signals so as to determine a property of a thin film layer at the surface of the sample.

13. The apparatus according to claim 8, wherein the signal processor is adapted to find a first elevation angle at which the first ratio has a given value and a second elevation angle at which the second ratio has the given value, and to determine the elevation angle of the tangent to the surface by taking an average of the first and second elevation angles.

14. The apparatus according to claim 13, wherein the signal processor is adapted to take a difference between the first and second elevation angles so as to determine the minimum elevation angle below which the shutter cuts off the radiation.

* * * * *